United States Patent
Joensen et al.

(10) Patent No.: US 9,611,202 B2
(45) Date of Patent: Apr. 4, 2017

(54) PROCESS FOR THE PREPARATION OF DIMETHYL ETHER

(71) Applicant: Haldor Topsoe A/S, Kgs. Lyngby (DK)

(72) Inventors: Finn Joensen, Hørsholm (DK); Jorgen Madsen, Hillerod (DK); Poul Erik Højlund Nielsen, Fredensborg (DK)

(73) Assignee: Haldor Topsoe A/S, Lyngby (DK)

( * ) Notice: Subject to any disclaimer, the term of this patent is extended or adjusted under 35 U.S.C. 154(b) by 32 days.

(21) Appl. No.: 14/424,522

(22) PCT Filed: Aug. 14, 2013

(86) PCT No.: PCT/EP2013/066979
§ 371 (c)(1),
(2) Date: Feb. 27, 2015

(87) PCT Pub. No.: WO2014/032973
PCT Pub. Date: Mar. 6, 2014

(65) Prior Publication Data
US 2015/0232401 A1    Aug. 20, 2015

(30) Foreign Application Priority Data
Aug. 31, 2012 (EP) .................. PCT/EP2012/067012

(51) Int. Cl.
C07C 41/42    (2006.01)
C07C 41/09    (2006.01)

(52) U.S. Cl.
CPC .............. *C07C 41/09* (2013.01); *C07C 41/42* (2013.01)

(58) Field of Classification Search
None
See application file for complete search history.

(56) References Cited

U.S. PATENT DOCUMENTS

2009/0054539 A1*  2/2009  Madsen .................. C07C 41/01
                                                         518/711

FOREIGN PATENT DOCUMENTS

EP    2028173 A1    2/2009
JP    2004-91327    3/2004

OTHER PUBLICATIONS

Machine translation fro JP2004-091327.*

* cited by examiner

*Primary Examiner* — Yong Chu
*Assistant Examiner* — Ana Z Muresan
(74) *Attorney, Agent, or Firm* — Blank Rome LLP

(57) ABSTRACT

Process for the preparation of dimethyl ether product by catalytic conversion of synthesis gas to dimethyl ether comprising the steps of contacting a stream of synthesis gas comprising carbon dioxide in a dimethyl ether synthesis step in one or more reactors and with one or more catalysts active in the formation of methanol and dehydration of methanol to dimethyl ether and forming a product mixture comprising dimethyl ether, carbon dioxide and unconverted synthesis gas; cooling and separating the product mixture into a first liquid phase comprising dimethyl ether and carbon dioxide being dissolved in the formed dimethyl ether, and into a first gaseous phase comprising unconverted synthesis gas containing carbon monoxide and carbon dioxide; passing the first liquid phase to a scrubbing zone and contacting the phase with a liquid sorbent being effective in absorption of carbon dioxide; and withdrawing a dimethyl ether product being depleted in carbon dioxide from the scrubbing zone.

9 Claims, 2 Drawing Sheets

PROCESS FOR THE PREPARATION OF DIMETHYL ETHER

Figure 1:
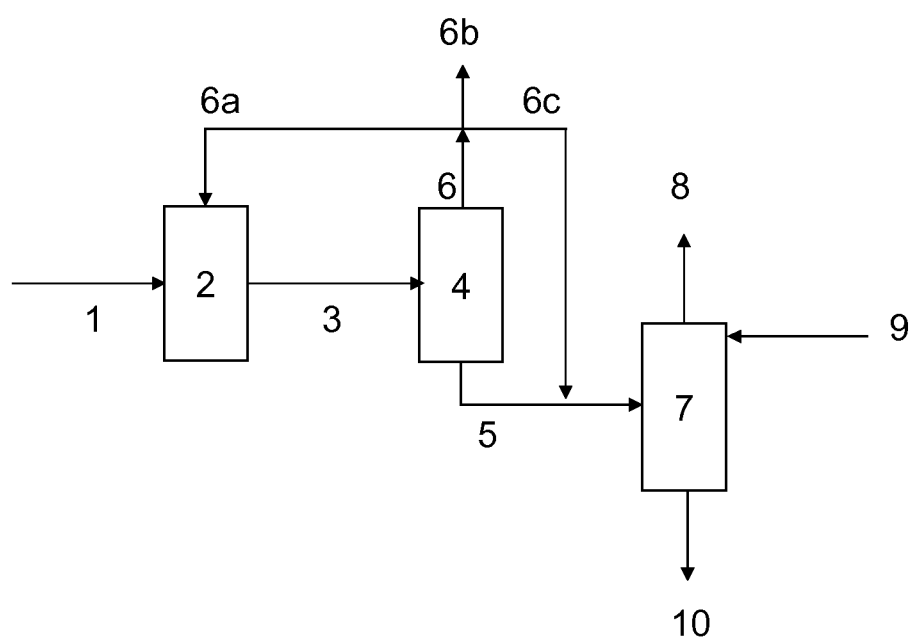

The invention concerns a process for preparation of dimethyl ether (DME) from synthesis gas. In particular, the invention concerns an improved dimethyl ether synthesis process by utilising chemical wash of raw product effluent from the ether synthesis step for the removal of carbon dioxide from the raw product to improve process yield and the final purification of produced dimethyl ether.

The process of the invention concerns purification of dimethyl ether being produced from carbon oxides and hydrogen containing synthesis gas.

The conversion of synthesis gas to dimethyl ether is carried out in one or more reactors, in which synthesis gas is catalytically converted to methanol shown in equation (1) and dimethyl ether as shown in equation (2). The shift reaction also takes place and is shown in equation (3).

$$CO + 2H_2 \rightarrow CH_3OH \quad (1)$$

$$2CH_3OH \rightarrow CH_3OCH_3 + H_2O \quad (2)$$

$$CO + H_2O \rightarrow CO_2 + H_2 \quad (3)$$

High conversion of synthesis gas is obtained when dimethyl ether is prepared at a stoichiometric ratio between hydrogen and carbon monoxide equal to or lower than two, and particularly high conversion is obtained at a H2:CO ratio equal to about one. At lower ratios less dimethyl ether is produced. At these conditions ($H_2/CO \approx 1$) the overall reaction takes place essentially according to equation (4):

$$3H_2 + 3CO \rightarrow CH_3OCH_3 + CO_2 \quad (4)$$

Thus, the reactor effluent will typically contain DME and $CO_2$ along with unconverted $H_2$ and CO. Carbon dioxide is soluble in dimethyl ether, and in order to obtain the dimethyl ether product with a required purity it is necessary to remove the carbon dioxide being present in the synthesis gas and formed in the reaction of carbon monoxide and hydrogen to dimethyl ether. Additionally, when carbon dioxide is removed the composition of the unconverted synthesis gas is close to that of the make up synthesis gas used to prepare dimethyl ether, which is an additional advantage, because it may be recycled directly to the dimethyl ether synthesis reactor.

Removal of carbon dioxide from the dimethyl ether product downstream the synthesis reactor can become very costly. Three basic processes for disposing of carbon dioxide are known. In the first process dimethyl ether is synthesized according to reactions (1) to (3) above. A mixed effluent stream comprising unreacted synthesis gas together with any carbon dioxide present is then separated from the dimethyl ether product, which also contains some unreacted methanol. The separated synthesis gas and carbon dioxide stream is recycled to the synthesis gas process stream entering the reactor. This process may conveniently be applied in a hydrogen rich synthesis gas having for instance a ratio between hydrogen and carbon monoxide above 5.

In the second known process a mixed effluent stream comprising unreacted synthesis gas together with carbon dioxide is separated from the dimethyl ether product. However, carbon dioxide is then subsequently separated from the synthesis gas. This can be done by washing this stream with for instance a suitable amine compound such as methyl diethanol amine, MDEA. The synthesis gas stream which is free of carbon dioxide is then recycled to the synthesis gas process stream entering the reactor. The carbon dioxide obtained may be employed in other processes for instance in the preparation of synthesis gas from natural gas by autothermal carbon dioxide reforming.

In the third known process only synthesis gas is separated from the dimethyl ether product and carbon dioxide. The dimethyl ether product thus contains both methanol and carbon dioxide. The separated synthesis gas is recycled to the synthesis gas process stream entering the reactor.

Various solvents are known in the prior art for removing carbon dioxide from mixtures with synthesis gas. The choice of solvent is dependent on the ability to dissolve dimethyl ether and carbon dioxide and the ideal solvent should have a high solubility for carbon dioxide and a low volatility.

U.S. Pat. No. 5,908,963 discloses a process for the preparation of dimethyl ether from synthesis gas in which synthesis gas is separated from dimethyl ether product and recycled to the synthesis gas process stream entering the dimethyl ether synthesis loop. The presence of excess methanol in the dimethyl ether product is the focus of the disclosed process and the removal of carbon dioxide is not addressed.

U.S. Pat. No. 6,458,856 discloses a one-step catalytic conversion process for dimethyl ether preparation. After catalytic conversion of synthesis gas to dimethyl ether the effluent from the reactor is processed into a vapour mixture comprising dimethyl ether, carbon dioxide and unconverted synthesis gas. The vapour mixture is scrubbed using a scrubbing solvent to separate both dimethyl ether and carbon dioxide from unconverted synthesis gas and the dimethyl ether is subsequently separated from the carbon dioxide. The scrubbing solvent comprises a mixture of dimethyl ether and methanol. The unconverted synthesis gas is recycled to the dimethyl reactor.

This reference also discloses prior art in which scrubbing solvents such as methanol, water, methanol/water mixtures, dimethyl ether or ethanol are used.

Dimethyl ether is a good solvent for carbon dioxide but is very volatile, whereas methanol is a poorer solvent for carbon dioxide than dimethyl ether but has the advantage of being less volatile. A process for preparing dimethyl ether from synthesis gas which makes use of a solvent having high solubility for carbon dioxide and simultaneously low volatility is therefore desirable.

JP 2004 091327 A also describes a process involving withdrawal of $CO_2$ by absorption in dimethyl ether in a process where dimethyl ether is cooled to reduce the volatility of dimethyl ether.

U.S. Pat. No. 7,652,176 discloses a process for the preparation of dimethyl ether from synthesis gas, in which a product mixture comprising dimethyl ether, carbon dioxide and unconverted synthesis gas is treated in a scrubbing zone with a liquid solvent being rich in potassium carbonate or amine. Carbon dioxide is thereby selectively removed from the dimethyl ether product by contact with the liquid solvent.

A problem can arise at high concentrations of carbon monoxide in the effluent from the dimethyl ether synthesis. Carbon monoxide reacts with amines in liquid amine-based solvents to form carbamates, which precipitate in the scrubbing zone, when the solution becomes supersaturated with the carbamates. In case of liquid solvents being rich in carbonates, e.g. potassium carbonate, part of the carbon monoxide may react to form formates, e.g. potassium formate. The references above are silent about formation of carbamates and formates.

It is thus the general object of the invention to provide an improved dimethyl ether synthesis process utilising a chemical carbon dioxide absorption process for removal of carbon dioxide being in a dimethyl ether synthesis product without the above problems, by reducing the carbon monoxide concentration in the feed to the scrubbing zone.

The invention provides a process for the preparation of dimethyl ether product by catalytic conversion of synthesis gas to dimethyl ether comprising the steps of contacting a stream of pressurised synthesis gas in a dimethyl ether synthesis step in one or more reactors and with one or more catalysts active in the formation of methanol and dehydration of methanol to dimethyl ether and forming a product mixture comprising dimethyl ether, carbon dioxide and unconverted synthesis gas; cooling and separating the product mixture into a first liquid phase comprising dimethyl ether and carbon dioxide being dissolved in the formed dimethyl ether, and into a first gaseous phase comprising unconverted synthesis gas containing carbon monoxide and carbon dioxide; passing the first liquid phase to a scrubbing zone and contacting the phase with a liquid sorbent being effective in absorption of carbon dioxide; and withdrawing a dimethyl ether product depleted in carbon dioxide from the scrubbing zone. The effect of separating the product mixture in a simple gas/liquid separator prior to scrubbing is that more CO is withdrawn in the gaseous phase, compared to $CO_2$ which is dissolved in liquid dimethyl ether. In this way the scrubbing process of dimethyl ether must remove less CO, with less risk of formate formation.

In a further embodiment the process comprises the further step of depressurizing the first liquid phase to form a second liquid phase and a second gaseous phase prior to passing the combined second liquid phase and the second gaseous phase to the scrubbing zone, with the associated benefit of depressurizing providing cooling of the liquid and gaseous phases, thus assisting a more efficient scrubbing process.

In a further embodiment the second liquid phase is introduced to the scrubbing zone at a position above the position of introduction of the second gaseous phase, with the associated benefit of cooling the scrubbing liquid by the heat of evaporation.

In a further embodiment the liquid solvent contains potassium carbonate or amine, with the associated benefit of—providing a liquid solvent with good $CO_2$ absorption capacity and low volatility.

In a further embodiment the process comprises the further step of subjecting the dimethyl ether product being withdrawn from the scrubbing zone to a distillation step, with the associated benefit of withdrawing liquid impurities such as methanol.

In a further embodiment the process comprises the further step of recycling at least a part of the first pressurised gaseous phase to the dimethyl ether synthesis step, with the associated benefit of increasing the overall conversion of H2 and CO and, thereby, further reducing the amount of CO directed to the scrubber.

In a further embodiment the methanol having been separated from the dimethyl ether in the distillation step are recycled to the dimethyl ether synthesis step, with the associated benefit of providing raw material for dimethyl ether synthesis.

In a further embodiment the methanol having been separated from the dimethyl ether in the distillation step are passed to a second dimethyl ether synthesis step for further conversion of methanol to dimethyl ether, with the associated benefit of providing raw material for a more efficient dimethyl ether synthesis.

In a further embodiment a dimethyl ether product stream of the second dimethyl ether synthesis step is recycled to the distillation step to separate water and methanol from dimethyl ether with the associated benefit of utilizing a single distillation step for both dimethyl ether produced in a first and a second dimethyl ether synthesis step.

In a further embodiment unconverted hydrogen and carbon monoxide having been separated from the dimethyl ether product are recycled to the dimethyl ether synthesis step, with the associated benefit of providing efficient use of available raw materials.

Any amounts of unconverted synthesis gas leaving the scrubbing zone with the CO2-depleted dimethyl ether product is preferably separated and recycled to the DME synthesis.

Liquid solvents being particularly suitable for use in the invention are selected from amine-based solvents and aqueous solvents containing potassium carbonate as used in the per se known Benfield™, Vetrocoke™ or Catacarb™ processes.

In order to obtain reasonable conversion rate and yield, the dimethyl ether synthesis from synthesis gas has to be performed at elevated pressure. At 7 MPa more than 80% conversion can realised and at 13 MPa more than 90%.

When performing the ether synthesis at high pressure, subsequent removal of carbon dioxide from the resulting pressurized reaction product may result in partial loss of dimethyl ether by dissolution of the ether into the liquid solvent employed in the carbon dioxide scrubber.

It is thus preferred to include in the process of the invention the further step of depressurizing the first pressurized liquid phase prior to passing the phase to the scrubbing zone.

When depressurizing the pressurized liquid phase the liquid phase splits into a gaseous and a liquid phase.

Thus, in a specific embodiment the first pressurized liquid phase is depressurized to obtain a second liquid phase with dimethyl ether and carbon dioxide dissolved in the liquid dimethyl ether and a second gaseous phase with a mixture of dimethyl ether and carbon dioxide.

The temperature decrease associated with depressurizing the first liquid phase in order to obtain the second liquid phase and the second gaseous phase serves as a convenient way of cooling the scrubbing zone, thereby facilitating the absorption.

The first pressurized liquid phase obtained by cooling the product mixture effluent from the DME reactor typically contains minor amounts of methanol and water. When passing the product mixture to the scrubbing zone, methanol and water will dissolve in the scrubbing solvent from which it may be recovered by conventional means, such as stripping or distillation. Recovered methanol may conveniently be recycled to the dimethyl ether synthesis step or it may be dehydrated into dimethyl ether in a separated step.

Figure 2:
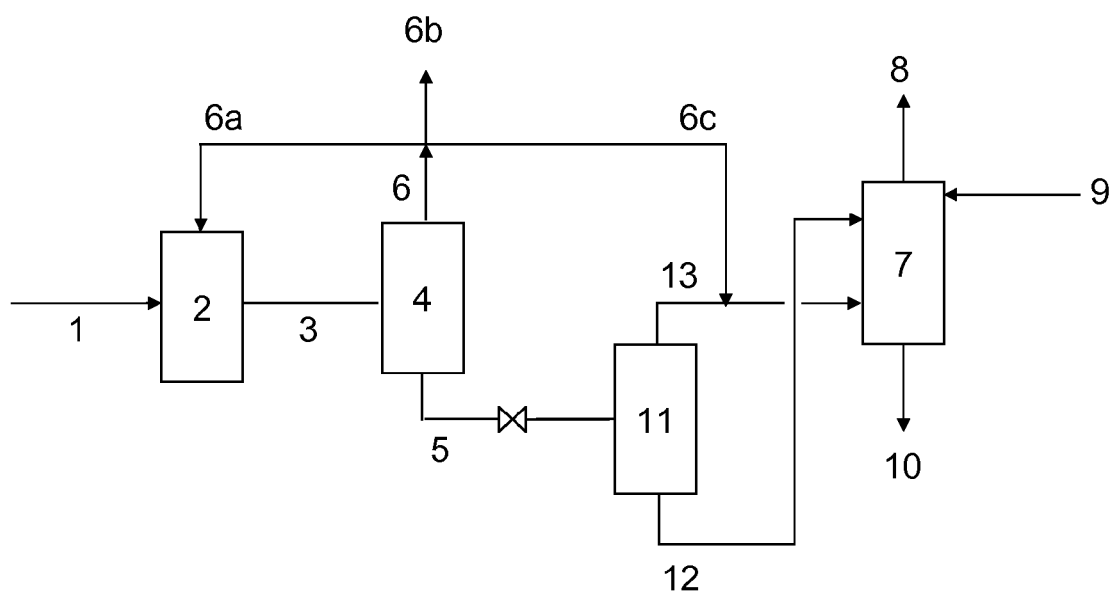

The invention is described in greater detail below with reference to the accompanying drawings, in which FIG. 1 shows the general process steps in the preparation of dimethyl ether from synthesis gas, and FIG. 2 shows a simplified flow diagram of a specific embodiment of the invention.

Synthesis gas 1, having a H2:CO ratio of about one, is sent to DME synthesis reactor 2 for catalytic conversion to methanol and DME according to reactions (1) and (2). The shift reaction also takes place according to reaction (3).

The effluent from DME synthesis reactor 2 contains product mixture 3, which comprises a mixture of dimethyl ether, carbon dioxide and unconverted synthesis gas. Product mixture 3 is cooled and passed to separator 4 forming a liquid phase 5 comprising the dimethyl ether product and CO2 dissolved therein, and a gaseous phase 6 comprising unconverted synthesis gas H2, CO, CO₂ and DME. Part of the gaseous phase leaving the separator may be recycled through line 6a to the DME synthesis reactor, the remainder being purged through line 6b or passed through line 6c to scrubbing zone 7 for recovery of DME values contained in the stream, either by addition to stream 5 (as shown in FIG. 1) or by introduction as a separate stream.

The liquid phase is passed as stream 5 to absorber unit 7 in which it is contacted with an amine solution or an aqueous solution 9 containing typically 20 to 40 wt % potassium carbonate for the removal of CO2 to obtain a product stream of DME 8 and a CO2-rich (as hydrogen carbonate) stream 10. The DME product stream 8 will typically contain additional components such as methanol and methyl ethyl ether, hydrogen and carbon monoxide and may be subjected to further purification by conventional means such as distillation and/or adsorption. The amounts of hydrogen and carbon monoxide recovered by the further purification steps may advantageously be recycled (not shown) to the oxygenate reactor 2. Likewise, amounts of methanol recovered, both in the step(s) of further purification and during regeneration of the absorption liquid, may advantageously be recycled to the oxygenate reactor or be converted into DME by conventional means in a separate step and recycled to the absorber unit 7.

FIG. 2 shows a simplified flow diagram of a specific embodiment of the invention. The flow diagram shown in FIG. 2 is similar to that of FIG. 1, the only difference being that the liquid product stream 5 is depressurized and, prior to being introduced to the absorber 7, the depressurized product stream is passed to a separator 11 dividing the product stream into a liquid stream 12 and a gaseous stream 13. Streams 12 and 13 are passed to the absorber 7, but the liquid stream 12 is introduced to the absorber at a position above the position of introduction of the gaseous stream 13. The gas stream 6c is also depressurized before being passed to the scrubbing zone.

Example 1

This is a comparative example according to prior art disclosed in U.S. Pat. No. 7,652,176 and does not feature any separation step prior to introducing the product stream to the scrubbing zone.

A synthesis gas having the composition 1 in Table 1 is passed to a DME synthesis reactor for catalytic conversion in a boiling water reactor at 8 MPa to methanol and DME according to reactions (1) to (3), producing a product stream 2 to be introduced, after cooling, to a scrubbing zone rich in potassium carbonate or amine.

TABLE 1

| (mol %) | 1 | 2 |
|---|---|---|
| T [° C.] | 200 | 250 |
| P [MPa] | 8 | 8 |
| H2 | 50.0 | 12.9 |
| CO | 48.0 | 11.4 |
| CO2 | 2.0 | 38.6 |
| H2O |  | 0.7 |
| MeOH |  | 2.0 |
| DME |  | 34.4 |
| kmol/h | 100.0 | 41.4 |

Example 2

This is an example according to an embodiment of the invention as shown in FIG. 1 and featuring a cooling and condensation step prior to introducing the liquid phase to the scrubbing zone rich in potassium carbonate or amine. Stream compositions are shown in Table 2, the stream numbers refer to FIG. 1. The synthesis gas 1 has the same composition and is converted under the same conditions as in comparative example 1.

TABLE 2

| (mol %) | 1 | 3 | 5 | 6a | 6b | 6c | 5 + 6c |
|---|---|---|---|---|---|---|---|
| T [° C.] | 200 | 250 | 30 | 30 | 30 | 30 | 30 |
| P [MPa] | 8 | 8 | 8 | 8 | 8 | 8 | 8 |
| H2 | 50.0 | 13.1 | 1.3 | 28.1 | 28.1 | 28.1 | 9.3 |
| CO | 48.0 | 11.2 | 3.0 | 21.8 | 21.8 | 21.8 | 8.6 |
| CO2 | 2.0 | 41.7 | 41.0 | 42.5 | 42.5 | 42.5 | 41.4 |
| H2O |  | 0.7 | 1.3 |  |  |  | 1.0 |
| MeOH |  | 2.0 | 3.5 | 0.1 | 0.1 | 0.1 | 2.5 |
| DME |  | 31.3 | 49.9 | 7.5 | 7.5 | 7.5 | 37.3 |
| kmol/h | 100.0 | 49.4 | 27.6 | 10.0 | (0.0) | 11.7 | 39.3 |

In contrast to comparative example 1, example 2 shows a reduction in the carbon monoxide concentration of the gas being passed to the scrubbing zone from to 11.4 (Example 1) to 8.6 mol % (combining streams 5 and 6c) thus reducing the degradation of the scrubbing solvent as mentioned in the hereinbefore.

Example 3

This example is similar to example 2, except that the recycle stream 6a has been increased from 10 kmol/h (R/M=0.1) to 50 kmol/h (R/M=0.5), where R/M denotes the recycle to makeup gas ratio. Stream data are shown in Table 3.

TABLE 3

| (mol %) | 1 | 3 | 5 | 6a | 6b | 6c | 5 + 6c |
|---|---|---|---|---|---|---|---|
| T [° C.] | 200 | 250 | 30 | 30 | 30 | 30 | 30 |
| P [MPa] | 8 | 8 | 8 | 8 | 8 | 8 | 8 |
| H2 | 50.0 | 11.2 | 0.8 | 17.7 | 17.7 | 17.7 | 2.3 |
| CO | 48.0 | 12.6 | 2.3 | 18.9 | 18.9 | 18.9 | 3.8 |
| CO2 | 2.0 | 51.7 | 45.3 | 55.6 | 55.6 | 55.6 | 46.2 |
| H2O |  | 0.7 | 1.8 |  |  |  | 1.6 |
| MeOH |  | 1.6 | 4.2 | 0.1 | 0.1 | 0.1 | 3.8 |
| DME |  | 22.2 | 46.8 | 7.7 | 7.7 | 7.7 | 42.3 |
| kmol/h | 100.0 | 86.1 | 32.8 | 50.0 | (0.0) | 3.3 | 36.5 |

Example 3 shows that the concentration of carbon monoxide in the product stream (5+6c) passed to the scrubber zone, may be controlled/reduced by adjusting/inreasing the recycle ratio. In Example 3 the carbon monoxide concentration of the gas being passed to the scrubbing zone has been further reduced from 8.6 (Example 2) to 3.8 mol % (by combination of streams 5 and 6c).

Example 4

This is an example of a preferred embodiment of the process according to invention, where the liquid phase is depressurized followed by a separation step as shown in FIG. 2. The synthesis gas 1 has the same composition and is converted under the same pressure and temperature as in comparative example 1. Therefore, the composition, flow, pressure and temperature of stream number 1, 3, 5, 6a and 6b are identical to those shown in Table 3. Stream compositions, pressure and temperature of stream 5 and the depressurized streams 6c, 12 and 13 are shown in Table 4. The stream numbers refer to FIG. 2.

TABLE 4

| (mol %) | 5 | 6c | 12 | 13 | 6c + 13 | 6c + 12 + 13 |
|---|---|---|---|---|---|---|
| T [° C.] | 200 | −18 | 4.4 | 4.4 | 1.4 | 2.7 |
| P [MPa] | 8 | 1 | 1 | 1 | 1 | 1 |
| H2 | 0.8 | 17.7 | | 1.5 | 4.2 | 2.3 |
| CO | 2.3 | 18.9 | 0.1 | 4.4 | 6.8 | 3.8 |
| CO2 | 45.3 | 55.6 | 18.8 | 70.7 | 68.2 | 46.2 |
| H2O | 1.8 | | 3.6 | | | 1.6 |
| MeOH | 4.2 | 0.1 | 8.4 | 0.1 | 0.1 | 3.8 |
| DME | 46.8 | 7.7 | 69.2 | 23.2 | 20.7 | 42.3 |
| kmol/h | 32.8 | 3.3 | 16.1 | 16.7 | 20.0 | 36.5 |

Example 4 illustrates a preferred embodiment wherein the process streams 6, 12 and 13 are cooled by depressurization, before passing the streams to the scrubbing zone, thus achieving a cooling effect in the scrubbing zone which improves the absorption of CO2.

The invention claimed is:

1. Process for the preparation of dimethyl ether product by catalytic conversion of synthesis gas to dimethyl ether comprising the steps of:

contacting a stream of synthesis gas in a dimethyl ether synthesis step in one or more reactors and with one or more catalysts active in the formation of methanol to dimethyl ether and forming a product mixture comprising dimethyl ether, carbon dioxide and unconverted synthesis gas;

reducing the carbon monoxide content of the product mixture by cooling and separating the product mixture into a first liquid phase at a temperature of about 30° C. comprising dimethyl ether and carbon dioxide dissolved in the formed dimethyl ether and into a first pressurized gaseous phase comprising unconverted synthesis gas containing carbon monoxide and carbon dioxide;

passing the cooled first liquid phase to a first scrubbing zone and contacting the first liquid phase with a liquid sorbent consisting essentially of an amine or carbonate rich solvent to remove carbon dioxide and form a scrubbed liquid phase containing a dimethyl ether product depleted of carbon dioxide and formates and/or carbamates;

passing the scrubbed liquid phase to a second scrubbing zone; and selectively: (1) recycling the first pressurized gaseous phase to the one or more reactors, (2) purging the first pressurized gaseous phase, or (3) passing the first pressurized gaseous phase to the second scrubbing zone.

2. The process of claim 1, comprising the further step of depressurizing the first liquid phase to form a second liquid phase and a second gaseous phase prior upstream of the second scrubbing zone, and separately feeding the second liquid phase and second gaseous phase to the second scrubbing zone.

3. The process of claim 2, wherein the second liquid phase is introduced to the scrubbing zone at a position above the position of introduction of the second gaseous phase.

4. The process of claim 1, comprising the further step of subjecting the dimethyl ether product being withdrawn from the second scrubbing zone to a distillation step.

5. The process of claim 1, comprising the further step of recycling at least a part of the first pressurized gaseous phase to the dimethyl ether synthesis step.

6. The process of claim 4, wherein the methanol having been separated from the dimethyl ether in the distillation step are recycled to the dimethyl ether synthesis step.

7. The process of claim 4, wherein the methanol having been separated from the dimethyl ether in the distillation step are passed to a second dimethyl ether synthesis step for further conversion of methanol to dimethyl ether.

8. The process of claim 6, wherein a dimethyl ether product stream of the second dimethyl ether synthesis step is recycled to the distillation step to separate water and methanol from dimethyl ether.

9. The process of claim 1, wherein unconverted hydrogen and carbon monoxide having been separated from the dimethyl ether product are recycled to the dimethyl ether synthesis step.

* * * * *